United States Patent [19]

Talebian et al.

[11] Patent Number: 4,946,954

[45] Date of Patent: Aug. 7, 1990

[54] PLATINUM PHARMACEUTICAL AGENTS

[75] Inventors: Abdolhossen Talebian, Herndon; Dianna C. Green, Falls Church, both of Va.; Philip S. Schein, Bryn Mawr, Pa.

[73] Assignee: Georgetown University, Washington, D.C.

[21] Appl. No.: 301,773

[22] Filed: Jan. 26, 1989

Related U.S. Application Data

[63] Continuation-in-part of Ser. No. 297,368, Jan. 17, 1989, which is a continuation-in-part of Ser. No. 143,761, Jan. 14, 1988, which is a continuation-in-part of Ser. No. 74,825, Jul. 17, 1987, abandoned.

[51] Int. Cl.$^5$ ..................... C07H 15/00; C07H 23/00
[52] U.S. Cl. .................................... 536/121; 536/17.1
[58] Field of Search ............................. 536/121, 17.1

[56] References Cited

U.S. PATENT DOCUMENTS 4,284,579  8/1981  Meischen et al. ............... 260/429 R
4,551,524  11/1985  Kidani ................................. 536/121
4,575,550  3/1986  Totani ................................. 536/121

FOREIGN PATENT DOCUMENTS 284197  9/1988  European Pat. Off. .

OTHER PUBLICATIONS

O. Gandolfi et al., "Aminomalonato(1,2-Diaminocyclohexane)Platinum(II)," *Inorganica Chimica Acta*, vol. 135, pp. 27-31, 1987.

M. P. Hacker et al., "Water-Soluble N-Substituted Iminodiacetato(1,2-Diaminocyclohexane)-Platinum (II) Complexes as Potential Antitumor Agents," *Cancer Research*, vol. 46, pp. 6250–6254, 1986.

L. A. Zwelling, "Cisplatin and New Platinum Analogs," *Cancer chemotherapy 7*, ch. 8, pp. 105–122, 1985.

*Primary Examiner*—Ronald W. Griffin
*Assistant Examiner*—Pamela S. Webber
*Attorney, Agent, or Firm*—Wegner & Bretschneider

[57] ABSTRACT

Platinum compounds useful in the treatment of cancer are disclosed. Compositions containing these compounds and methods of using the same are also discussed. Compounds having the formula

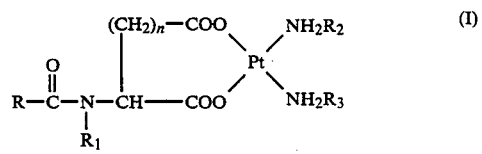

wherein n is 0 or 1 and when n is 1 $R_1$ is H or $C_1$–$C_4$ alkyl, R is non-substituted higher alkyl or mono or disaccharide or a derivative of a mono or disaccharide, when n is O, $R_1$ is H or $C_1$–$C_4$ alkyl, R is H, halogen, non-substituted $C_{1-20}$ alkyl, aryl, arlalkyloxy, mono or disaccharide, or a derivative of a mono or disaccharide, and $R_2$ and $R_3$ are selected from the group consisting of hydrogen, $C_1$–$^4$ alkyl or $R_2$ and $R_3$ or $R_2$ and $R_3$ together are linked to adjacent carbon atoms on a four, five or six membered ring structure, or $R_2$ and $R_3$ together form a fused or bicyclic ring with adjacent carbon atoms, or $R_2$ and $R_3$ together are a substituted or unsubstituted $C_{1-5}$ alkylene group; with the proviso that R and $R_1$ cannot both be hydrogen when n=0, or a pharmaceutically acceptable salt thereof, are particularly useful.

14 Claims, No Drawings

PLATINUM PHARMACEUTICAL AGENTS

This application is a continuation-in-part of Ser. No. 297,368 filed Jan. 17, 1989, which is a continuation-in-part of Ser. No. 143,761 U.S. Pat. No. 4,895,936 filed Jan. 14, 1988, which is a continuation-in-part of Ser. No. 074,825 filed July 17, 1987 now abandoned.

BACKGROUND OF THE INVENTION

Platinum anti-cancer agents are known in the literature. One of the most well publicized of the platinum anti-cancer agents is cis-diammine-dichloroplatinum (II), also known as cis-DDP and cisplatin. A discussion of cisplatin and its usefulness in the treatment of various types of cancer, such as testicular carcinoma, bladder cancer, ovarian cancer, and head and neck cancer can be found in Zwelling, *Cancer Chemotherapy*, 105–122 (1985).

Problems arise when such platinum agents are used in cancer treatment however. The toxicity of platinum to the bone marrow and kidneys precludes large sized dosages which can, in effect, render such treatment ineffective. Also, the overall desirability of and confidence in chemotherapy based upon known platinum active ingredients is decreased due to the drastic consequences to bone marrow and kidneys of the use of toxic levels of platinum.

SUMMARY OF THE INVENTION

The present invention is directed toward platinum anti-cancer agents having increased water solubility. Such an increase in water solubility aids the body in passing the platinum our of the system, thus preserving healthy bone marrow and kidneys. The water solubility of the platinum anti-cancer agents is enhanced by the presence of a mono or disaccharide group on the platinum active ingredient compound.

Pharmaceutical compositions containing the active ingredient and methods of treating carcinoma by administering said compositions to patients suffering from carcinoma are also

DETAILED DESCRIPTION OF THE INVENTION

In a first aspect of the present invention, there is provided a compound of the formula:

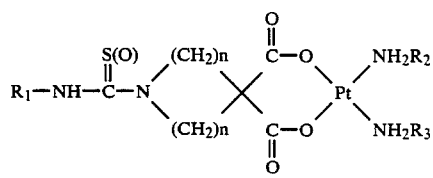

wherein n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure or a pharmaceutically acceptable salt thereof.

The symbol "(O)" next to the sulfur atom indicates that an oxygen atom may replace the sulfur atom in the structure of the present invention.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the first aspect of the present invention involves a compound of the formula (I), wherein $R_1$ is a mono or disaccharide or derivative thereof selected from the group consisting of glucose, galactose, mannose, glucosamine and galactosamine and derivatives thereof.

Another preferred embodiment of the first aspect of the present invention involves a compound of formula (I), wherein $R_2$ and $R_3$ are hydrogen.

Still another preferred embodiment of the first aspect of the present invention involves a compound of formula (I), wherein $R_2$ and $R_3$ together are linked to adjacent carbon atoms on a five or six membered ring structure.

Another preferred embodiment of the first aspect of the present invention involves a compound of the formula:

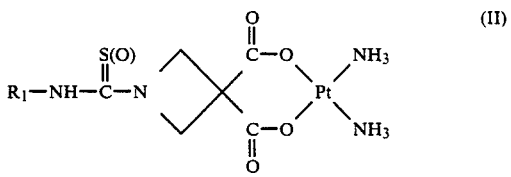

and $R_1$ is selected from the group comprising glucose, mannose, galactose, glucosamine, galactosamine and derivatives thereof.

Further preferred in a first aspect of the present invention is a compound, wherein the compound is of the formula:

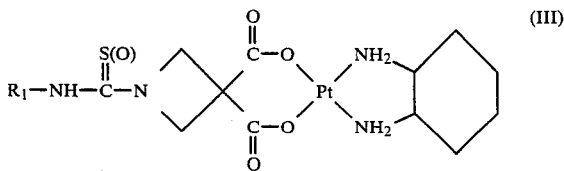

and $R_1$ is selected from the group comprising glucose, mannose, galactose, glucosamine, galactosamine and derivatives thereof.

Additionally preferred in the first aspect of the present invention is a compound, wherein the compound is of the formula:

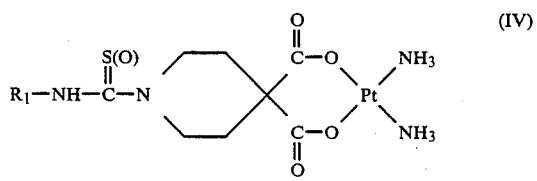

and $R_1$ is selected from the group comprising glucose, mannose, galactose, glucosamine, galactosamine and derivatives thereof.

Another preferred embodiment of the first aspect of the invention is a compound, wherein the compound is of the formula:

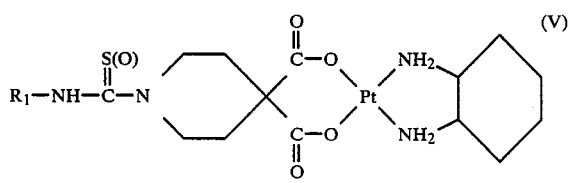

and $R_1$ is selected from the group comprising glucose, mannose, galactose, glucosamine, galactosamine and derivatives thereof.

A second aspect of the present invention involves a compound of the formula:

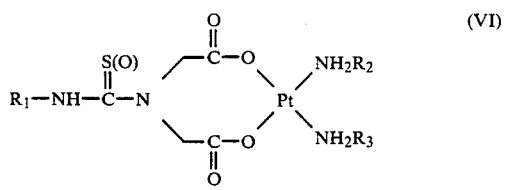

wherein $R_1$ is a mono or disaccharide or a derivative thereof, $R_2$ and $R_3$ are selected from the group consisting of hydrogen, $C_{1-4}$ alkyl or $R_2$ and $R_3$ or $R_2$ and $R_3$ together are linked to adjacent carbon atoms on a five or six membered ring structure
or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the second aspect of the present invention involves a compound of the formula (VI), wherein $R_1$ is a mono or disaccharide or derivative thereof selected from the group consisting of glucose, galactose, mannose, glucosamine and galactosamine and derivatives thereof.

Another preferred embodiment of the second aspect of the present invention involves a compound of formula (VI), wherein $R_2$ and $R_3$ are hydrogen.

Still another preferred embodiment of the second aspect of the present invention involves a compound of formula (VI), wherein $R_2$ and $R_3$ together are linked to adjacent carbon atoms on a five or six membered ring structure.

Further preferred in the second embodiment is a compound, wherein the compound is of the formula:

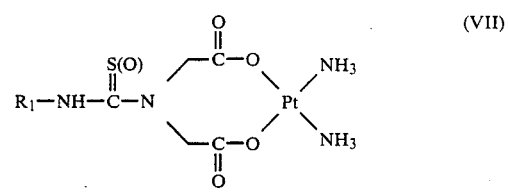

and $R_1$ is selected from the group comprising glucose, mannose, galactose, glucosamine, galactosamine and derivatives thereof.

Additionally preferred in the second embodiment is a compound, wherein the compound is of the formula:

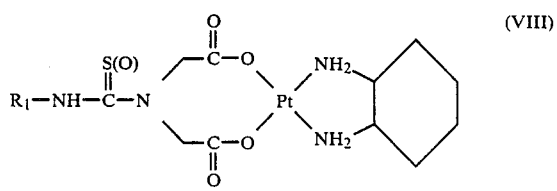

and $R_1$ is selected from the group comprising glucose, mannose, galactose, glucosamine, galactosamine and derivatives thereof.

Also preferred within the second aspect of the present invention is a compound of the formula:

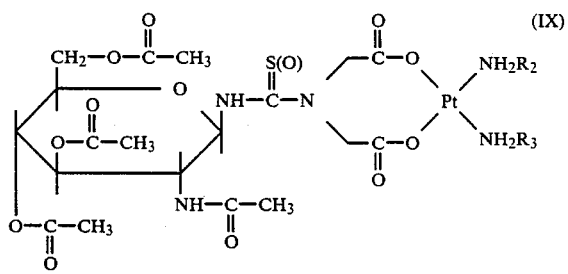

wherein $R_2$ and $R_3$ are as defined above.

In a third aspect of the present invention, there is provided a compound of the formula:

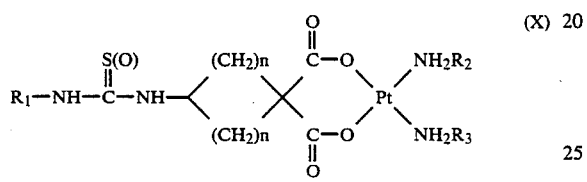

wherein n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of this aspect involves a compound, wherein said compound is of the formula:

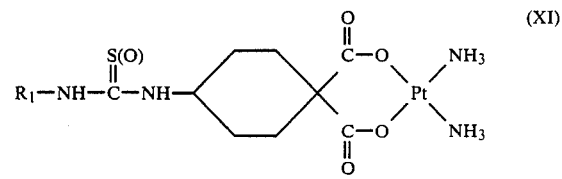

and $R_1$ is selected from the group comprising glucose, mannose, galactose, glucosamine, galactosamine and derivatives thereof.

An additional preferred embodiment of the present invention involves a compound, wherein said compound is of the formula:

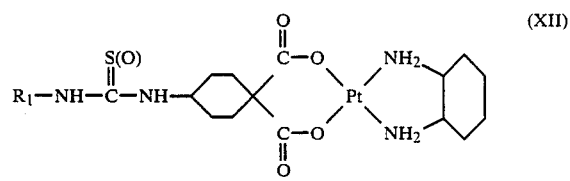

and $R_1$ is selected from the group comprising glucose, mannose, galactose, glucosamine, galactosamine and derivatives thereof.

In a fourth aspect of the present invention, there is provided a compound of the formula

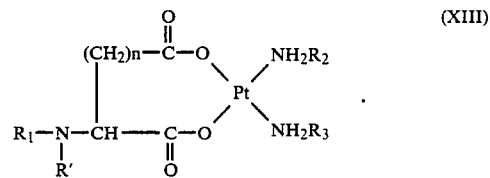

wherein n is 0 or 1, $R_1$ is selected from the group consisting of hydrogen, a mono or disaccharide or a derivative thereof linked to the nitrogen atom by a —NH-CO— amide moiety, an —NHCS— thioamide moiety, or a —CO— carbonyl moiety, R' is selected from the group consisting of hydrogen and $C_{1-4}$ alkyl, and $R_2$ and $R_3$ are selected from the group consisting of hydrogen, $C_{1-4}$ alkyl or $R_2$ and $R_3$ or $R_2$ and $R_3$ together are linked to adjacent carbon atoms on a four, five or six membered ring structure, or $R_2$ and $R_3$ together form a fused or bicyclic ring with adjacent carbon atoms; with the proviso that R' and $R_1$ cannot both be hydrogen when n=0, or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a fused or polycyclic ring there are contemplated rings of the following formulae:

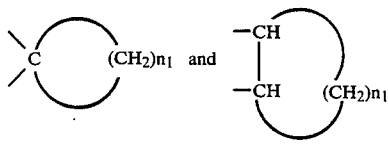

wherein $n_1$ is selected from 1, 2, 3, 4, 5 or 6.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the third aspect of the present invention involves a compound of the formula (X), wherein $R_1$ is a mono or disaccharide or derivative thereof selected from the group consisting of glucose, galactose, mannose, glucosamine and galactosamine and derivatives thereof.

Another preferred embodiment of this aspect of the present invention involves a compound of formula (X), wherein $R_2$ and $R_3$ are hydrogen.

Still another preferred embodiment of the fourth aspect of the present invention involves a compound of formula (X), wherein $R_2$ and $R_3$ together are linked to adjacent carbon atoms on a five or six membered ring structure.

Further preferred in this aspect is a compound, wherein the compound is of the formula:

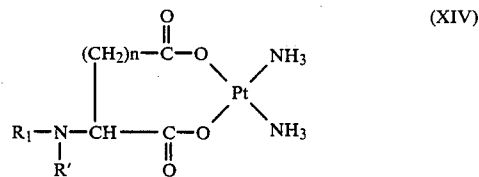

Also embodied in this aspect of the present invention is a compound, wherein the compound is of the formula:

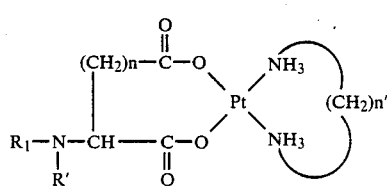

wherein n' is 1, 2 or 3.

A further preferred embodiment of the fourth aspect of the invention involves compounds of the formula:

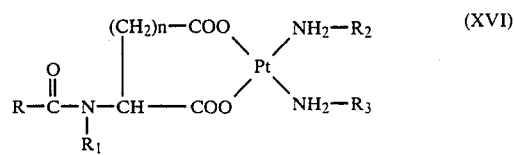

wherein when n=1, $R_1$ is H or $C_1$–$C_4$ alkyl R is non-substituted higher alkyl ($C_{10}$–$C_{20}$) or mono or disaccharide (including derivatives such as sugar alcohol, deoxy sugar, glyconic acid, glycuronic acid, glycoside, acetyl substituted, amino substituted, and N-acetyl substituted derivatives and the like)

and wherein when n=0, $R_1$ is H or $C_1$–$C_4$ alkyl

R is H, halogen, non-substituted alkyl ($C_1$–$C_2$), aryl, aralkyloxy, and mono or disaccharide, including the derivatives discussed above. In each case, $R_2$ and $R_3$ are as defined in formula XIII, or are linked together to form a $C_{1-5}$ substituted or non-substituted alkylene group, thus forming a 4 to 8 member ring with the platinum and nitrogens. Examples of suitable substituents include one or more of halogen, aryl and $C_{1-20}$ alkyl. One or more of the carbons of the $C_{1-5}$ group may be substituted.

The compounds of formula XVI in which R is higher alkyl ($C_{10-20}$) exhibit increased lipid solubility. Such compounds are therefore useful in treating cancers in fatty tissues, e.g., breast cancer. These compounds are also readily incorporated in liposomes, thus making feasible a liposome including platinum.

Another embodiment of this aspect of the present invention contemplates a compound, wherein $R_2$ and $R_3$ together form a fused or bicyclic ring with adjacent carbon atoms.

A preferred embodiment of the present invention involves a compound, wherein said compound is (L-aspartato-O,O')-(1,2-cyclohexanediammine-N,N')-platinum (II).

An additional embodiment involves a compound, wherein said compound is diammine-2-[[[[3,4,6-tri-O-acetyl-2-(N-acetylamino)-2-deoxy-alpha-D-glucopyranosyl]amino]thioxomethyl]amino]butanedioato-O,O']-platinum (II).

A further embodiment of the present invention involves a compound, wherein said compound is 2-[[[[3,4,6-tri-O-acetyl-2-(N-acetylamino)-2-deoxy-alpha-D-glucopyranosyl]amino]thioxomethyl]amino]-butanedioato-O,O']-(1,2-cyclohexanediammine-N,N')-platinum (II).

Further specific compounds within the embodiment of formula XVI include cis R,R-( acetamidomalonato-O,O')(1,2-cyclohexanediamine-N,N')platinum (II) ("AMP"), cis R,R-(formamidomalonato-O,O')(1,2-cyclohexanediamine-N,N')platinum II ("FMP"), diammine(acetamidomalonato-O,O')platinum (II), and (acetamidomalonato-O,O')(2,2-dimethyl-1,3-propanediamine-N,N')platinum (II). Although certain specific isomers have been included, e.g., the R,R form, other isomers are contemplated, as well as mixtures of isomers.

In accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (I) and a pharmaceutically acceptable carrier therefor The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, is of formula (I) and is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (I), and is such that $R_2$ and $R_3$ are hydrogen.

Still another preferred composition of the present invention involves a composition, wherein said compound is of formula (I) and is such that $R_2$ and $R_3$ together are linked to adjacent carbon atoms on a five or six membered ring structure.

Additional preferred compositions of the present invention involve compositions, wherein the active compound therein is a compound of formulae (II), (III), (IV) and (V).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (VI) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, and is of formula (VI) is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (VI) and is such that $R_2$ and $R_3$ are hydrogen.

Still another preferred composition the present invention involves a composition, wherein said compound is of formula (VI) and is such that $R_2$ and $R_3$ together are linked to adjacent carbon atoms on a five or six membered ring structure.

Additional preferred compositions of the present invention involve compositions, wherein the active compound therein is a compound of formulae (VII), (VIII) and (IX).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (X) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

Preferred compositions of the present invention involve compositions, wherein the active compound therein is a compound of formulae (XI) and (XII).

Moreover, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (XIII) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, and is of formula (XIII) is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (XIII) and is such that $R_2$ and $R_3$ are hydrogen.

Still another preferred composition the present invention involves a composition, wherein said compound is of formula (XIII) and is such that $R_2$ and $R_3$ together are linked to adjacent carbon atoms on a five or six membered ring structure.

Additional preferred compositions of the present invention involve compositions, wherein the active compound therein is a compound of formulae (XIV), (XV), and (XVI), (L-aspartato-O,O')-1(1,2-cyclohexanediammine)-N,N'-platinum (II),diammine-2[[[[-3,4,6-tri-O-acetyl-2-(N-acetylamino)-2-deoxy-alpha-D-glucopyranosyl]amino]thioxomethyl]amino]butanedioato-O,O']platinum (II), 2-[[[[3,4,6-tri-O-acetyl-2-(N-acetylamino)-2-deoxy-alpha-D-glucopyranosyl]amino]-thioxomethyl]amino]thioxomethyl]amino] butanedioato-O,O']-(1,2-cyclohexanediammine-N,N')-platinum (II), cis R,R-(acetamidomalonato-O,O')(1,2-cyclohexanediamine-N,N') platinum (II) ("AMP"), cis-R,R-(formamidomalonato-O,O')(1,2-cyclohexanediamine-N,N') platinum (II) ("FMP"), diammine (acetamidomalonato-O,O') platinum (II) and (acetamidomalonato-O,O')(2,2-dimethyl-1,3-propanediamine-N,N') platinum (II).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (I) and a pharmaceutically acceptable carrier thereof to a patient suffering from said ailments.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

A preferred method of the present invention involves the administration of a compound of formula (I), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (I), wherein said compound is such that $R_2$ and $R_3$ are hydrogen.

A further method of the present invention involves the administration of a compound of formula (I), wherein said compound is such that $R_2$ and $R_3$ together are linked to adjacent carbon atoms on a five or six membered ring structure.

Additional preferred methods of the present invention involve the administration of a compound, wherein the compound therein is a compound of formulae (II), (III), (IV), and (V).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (VI) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

A preferred method of the present invention involves the administration of a compound of formula (VI), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (VI), wherein said compound is such that $R_2$ and $R_3$ are hydrogen.

A further method of the present invention involves the administration of a compound of formula (VI), wherein said compound is such that $R_2$ and $R_3$ together are linked to adjacent carbon atoms on a five or six membered ring structure.

Additional preferred methods of the present invention involve administration of compounds, wherein the compound therein is a compound of formulae (VII), (VIII) and (IX).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (X) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

Additional preferred methods of the present invention involve administration of compounds, wherein the compound therein is a compound of formulae (XI) and (XII).

Still further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (XIII) and a pharmaceutically acceptable carrier therefor to a patient suffering from said ailments.

The administration can occur through oral, intraperitoneal, intramuscular and intravenous routes Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per m² body surface area of a patient. A preferred dosage of the active compound involves the administration of about 10 to about 200 mg per m² body surface area of a patient. A more preferred dosage of the active compound involves the administration of about 50 to about 150 mg per m² body surface area of a patient.

Another preferred method of the present invention involves the administration of a compound of formula (XIII), wherein said compound is such that R is a mono or disaccharide or derivative thereof selected from the group consisting of glucose, galactose, mannose, glucosamine and galactosamine and derivatives thereof.

Another preferred method of the present invention involves the administration of a compound of formula (XIII), wherein said compound is such that $R_2$ and $R_3$ are hydrogen.

A further method of the present invention involves the administration of a compound of formula (XIII), wherein said compound is such that $R_2$ and $R_3$ together are linked to adjacent carbon atoms on a five or six membered ring structure.

Additional preferred methods of the present invention involve the administration of a compound, wherein the compound therein is a compound of formulae (XIV), (XV) and (XVI), (L-aspartato-O,O')-(1,2-cyclohexanediammine)-N,N'-platinum (II), diammine-2-[[[[3,4,6-tri-O-acetyl-2-(N-acetylamino)-2-deoxy-alpha-D-glucopyranosyl]amino]thioxomethyl]amino]-butanedioato-O,O']-platinum (II), 2-[[[[3,4,6-tri-O-acetyl-2-(N-acetylamino)-2-deoxy-alpha-D-glucopyranosyl]amino]thioxomethyl]amino]butanedioato-O,O']-(1,2-cyclohexanediammine-N,N')-platinum (II), cis R,R-(acetamidomalonato-O,O')(1,2-cyclohexanediamine-N,N') platinum (II) ("AMP"), cis-R,R-(formamidomalonato-O,O')(1,2-cyclohexanediamine-N,N') platinum (II) ("FMP"). diammine (acetamidomalonato-O,O') platinum (II) and (acetamidomalonato-O,O')(2,2-dimethyl-1,3-propanediamine-N,N') platinum (II).

The thio compounds of formula (I) of the present invention may be prepared according to the following reaction scheme:

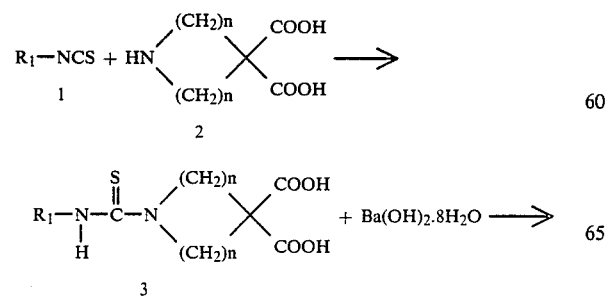

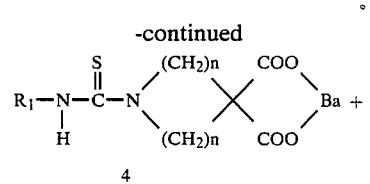

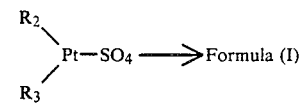

The oxo derivatives can be made in accordance with an analagous method with an $R_1$-NCO starting material.

The compound of formula (VI) may also be made in accordance with the above reaction scheme with the substitution of the following reactant 2 into the first reaction step.

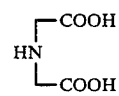

The compounds of the third aspect of the present invention can be prepared according to an analogous reaction mechanism utilizing a cycloalkyl containing starting material.

The compounds of formula (XIII) may be prepared in accordance with the following reaction scheme.

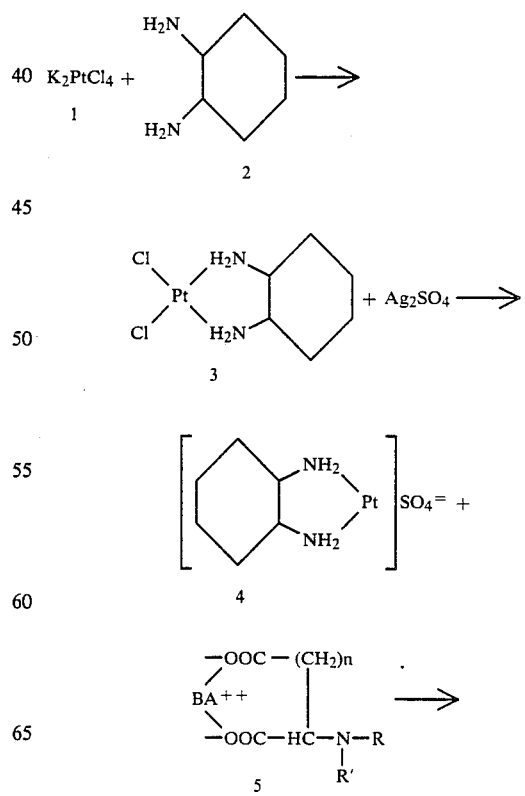

-continued

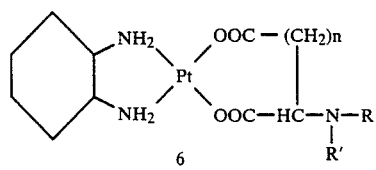

Similarly, the compounds of formula (XVI) of the present invention may be prepared according to the following reaction scheme:

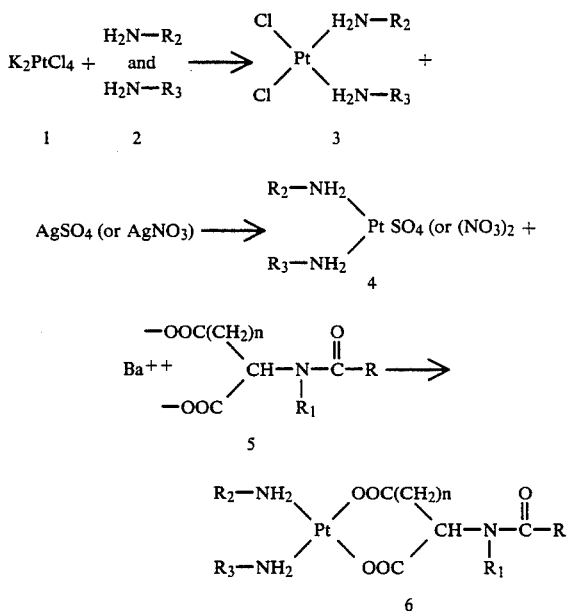

The following are exemplary of the present invention.

EXAMPLE I 1.2 g of 2-(N-acetylamino)-3,4,6-tri-O-acetyl-2deoxyglucopyranosyl isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cissulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of [[2-(N-acetylamino)-3,4,6-tri-O-acetyl-2-deoxyglucopyranosyl]amino]thioxomethyl]imino-diacetic acid.

EXAMPLE II

The compound of Example I is admixed with an isotonic solution to produce a dosage form suitable for intravenous administration. 130 mg/m$^2$ body surface area of a patient is administered to said patient through intravenous administration over a period of 24 hours.

EXAMPLE III 1.2 g of tetra-O-acetyl-D-mannopyranosyl-isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide 8H$_2$O. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammine-platinum(II) salt/complex of [[[tetra-O-acetyl-D-mannopyranosyl]amino]thioxomethyl]imino-diacetic acid.

EXAMPLE IV

The compound of Example III is admixed with an isotonic solution to produce a dosage form suitable for intramuscular administration. 80 mg/m$^2$ body surface area of a patient is administered to said patient through intramuscular administration daily.

EXAMPLE V 1.2 g of tetra-O-acetyl-D-galactopyranosyl-isothiocyanate in 5 ml acetonitrile is added to a solution of 0.413 of iminodiacetic acid and 1.12 ml of N,N-diisopropylethylamine in 25 ml of a water-acetonitrile mixture (1 1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide 8H$_2$O. The resultant is added to 0.4 grams of cissulfato cyclohexane-1,2-diammine-N,N'-platinum II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt-/complex of [[[tetra-O-acetyl-galactopyranosyl]amino]-thioxomethyl]imino-diacetic acid.

EXAMPLE VI

The compound of Example V is admixed with an isotonic solution to produce a dosage form suitable for intraperitoneal administration. 100 mg/m² body surface area of a patient is administered to said patient through intraperitoneal administration weekly.

EXAMPLE VII 1.2 g of 3,4,6-tri-O-acetyl-2-(N-acetylamino)-2-deoxy-alpha-D-glucopyranosyl-isothiocyanate in 5 ml acetonitrile is added to a solution of 0.413 g of iminodiacetic acid and 1.12 ml of N,N-diisoppropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cis-sulfato-amino-methylamino-N,N'-platinum(II) which is already in solution with 20 ml of water. This mixture is stirred at room temperature for 2 hours. Next the barium sulfate is filtered off, and the resulting filtrate is evaporated under reduced pressure to yield a amino-methylamino-N,N'-platinum(II) salt-/complex of [[[3,4,6-tri-O-acetyl-2-(N-acetylamino) 2-deoxy-alpha-D-glucopyranosyl]amino]thioxomethyl-]imino diacetic acid.

EXAMPLE VIII

The compound of Example VII is admixed with an hydroxypropylcellulose to form a dosage form suitable for oral administration. 120 mg/m² body surface area of a patient is administered to said patient through oral administration daily.

EXAMPLE IX 1.2 g of 3,4,6-tri-O-acetyl-2-(N-acetylamino)-2-deoxy-alpha-D-galactopyranosyl-isothiocyanate in 5 ml acetonitrile is added to a solution of 0.413 g of 4-amino-1,1-cyclohexanedicarboxylic acid and 1.12 ml of diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide 8H$_2$O. The resultant is added to 0.4 grams of cissulfato-cyclopentane-1,2-diammine-N,N'-platinum(II) which is already in solution with 20 ml of water. This mixture is stirred at room temperature for 2 hours. Next the barium sulfate is filtered off, and the resulting filtrate is evaporated under reduced pressure to yield a cyclopentane-1,2-diammineplatinum(II) salt-/complex of 4-[[[3,4,6-tri-O-acetyl-2-(N-acetylamino)-2-deoxy-alpha-D-galactopyranosyl]amino]thioxomethyl1,1-cyclchexanedicarboxylic acid.

EXAMPLE X

The compound of Example IX is admixed with an isotonic solution to produce a dosage form suitable for intravenous administration. 150 mg/m² body surface area of a patient is administered to said patient through intravenous administration after a period of 24 hours.

EXAMPLE XI 1.2 g of 2-(N-acetylamino)-3,4,6-tri-O-acetyl-2-deoxyglucopyranosyl isothiocyanate in 5 ml acetonitrile is added to a solution of 0.413 g of 3,3-trimethyleneimino dicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g cf this intermediate is admixed with 0.3 g barium hydroxide.8H$_2$O. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O-acetyl-2-deoxyglucopyranosyl-amino-thioxomethyl-3,3-trimethyleneimino-dicarboxylic acid.

EXAMPLE XII

The compound of Example XI is admixed with an isotonic solution to produce a dosage form suitable for intramuscular administration. 50 mg/m² body surface area of a patient is administered to said patient through intramuscular administration daily.

EXAMPLE XIII 1.2 g of tetra-O-acetyl-glucopyranosyl-isothiocyanate in 5 ml acetonitrile is added to a solution of 0.413 g of 4-amino-1,1-cyclohexanedicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cissulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of 4-[[(tetra-O-acetyl-alpha-D-glucopyranosyl)amino]thioxomethyl]amino]-1,1-cyclohexanedicarboxylic acid.

EXAMPLE XIV

The compound of Example XIII is admixed with an isotonic solution to produce a dosage form suitable for intraperitoneal administration. 150 mg/m$^2$ body surface area of a patient is administered to said patient through intraperitoneal administration every 3 weeks.

EXAMPLE XV 1.2 of 2-(N-acetylamino)-3,4,6-tri-O-acetyl-2-deoxyglucopyranosyl isothiocyanate in 5 ml acetonitrile is added to a solution of 0.413 g of 3,3-trimethyleneiminodicarboxylic acid and 1.12 ml of diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O -acetyl-2-deoxyglucopyranosyl-amino-thioxomethyl-3,3-trimethyleneimino-dicarboxylic acid.

EXAMPLE XVI

The compound of Example XV is admixed with glycerin monostearate to produce a dosage form suitable for oral administration. 70 mg/m$^2$ body surface area of a patient is administered to said patient through oral administration daily.

EXAMPLE XVII 1.2 g of tetra-O-acetyl-galactopyranosyl-isothiocyanate in 5 ml acetonitrile is added to a solution of 0.413 g of 3,3-trimethyleneiminodicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of tetra-O-acetyl-galactopyranosyl-amino-thioxomethyl-3,3-trimethyleneiminodicarboxylic acid.

EXAMPLE XVIII

The compound of Example XVII is admixed with glycerin monostearate to produce a dosage form for oral administration. 70 mg/m$^2$ body surface area of a patient is administered to said patient through oral administration daily.

EXAMPLE XIX 1.2 g of tetra-O-acetyl-glucopyranosyl isothiocyanate in 5 ml acetonitrile is added to a solution of 0.413 g of 4,4-piperidinedicarboxylic acid and 1 12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams cissulfato-cyclohexane-1,2-diammine-platinum-(II) which is already in solution with 20 ml of water. This mixture is stirred at room temperature for 2 hours. Next the barium sulfate is filtered off, and the resulting filtrate is evaporated under reduced pressure to yield a 1,2-cyclohexane-diammino-platinum(II) salt/complex of 4-[[(tetra-O-acetyl-glucopyranosyl)amino]thioxomethyl]amino]-4,4-piperidinedicarboxylic acid.

EXAMPLE XX

The compound of Example XV is admixed with hydroxypropylcellulose to produce a dosage form suitable for oral administration. 100 mg/m$^2$ body surface area of a patient is administered to said patient through oral administration daily.

EXAMPLE XXI

The cyclohexane-1,2-diammine-platinum(II) salt of 2-(acetylamino)-3,4,6-tri-O-acetyl-2-deoxy-glucopyranosyl-amino-thioxomethyl-imino diacetic acid and cisplatin were tested against murine P388 leukemia. The murine P388 leukemia system is known to be sensitive to cisplatin. The leukemia was maintained intraperitoneally in female DBA/2 mice.

Prior to administration, cisplatin was dissolved in ethanol. The solution was then adjusted to 5% ethanol, 95% sterile water The cyclohexane-1,2-diammineplatinum(II) salt of 2-(acetylamino)-3,4,6-tri-O-acetyl-2-deoxyglucopyranosylamino-thioxomethyl-imino diacetic acid was dissolved in sterile water at 4 degrees celsius immediately prior to administration.

Each compound was administered intraperitoneally to groups of $CD2F_1$ male mice on day 1 after intraperitoneal implantation of $1 \times 10^6$ P388 leukemia cells. P388 antileukemic activity for each compound was assessed by mean survival days and percentage increased life span (% ILS).

% ILS is calculated as follows:

%ILS = (T−C)/C × 100 wherein T is the mean survival days of the treated mice and C is the mean survival days of the untreated mice. The results of the experimentation are shown in the following table.

TABLE 1

| Compound | Dose | % ILS | Mean Survival (days) |
| --- | --- | --- | --- |
| cisplatin | 10 mg/kg | 83 | 17.4 |
| invention | 100 mg/kg | 80 | 17.1 |

EXAMPLE XXII

Preparation of Dicarboxylic Acid Ligand.

3,4,6-tri-O-acetyl-2-(acetylamino)-2-deoxyglucopyranosyl isothiocyanate is added to a solution of aspartic acid and N,N-diisopropylethylamine in a mixture of water-acetonitrile. The mixture is stirred at room temperature in the dark until thin-layer chromarography (chloroform:methanol 10:1) indicates reaction completion. Acetonitrile is removed and the water layer is basified with 10% $NaHCO_3$. The basic solution is extracted with 2×75 ml $CH_2Cl_2$, is acidified with 10% HCl and is extracted with 2×100 ml of ethyl acetate. The ethyl acetate layer is dried over anhydrous $Na_2SO_4$ and is evaporated to dryness to give 2-[[[3,4,6-tri-O-acetyl-2-(N-acetylamino)-2-deoxy-alpha-D-glucopyranosyl]amino]thioxomethyl]amino]butanedioic acid. X.p. 124–126.

EXAMPLE XXIII

Preparation of Cis-Sulfato-DACH-Platinum (II)

To a freshly prepared solution of $K_2PtCl_4$ is added an equimolar amount of 1,2-cyclohexanediamine in distilled water. This mixture is allowed to react at room temperature in a nitrogen atmosphere protected from light for 8 hours. The precipitate is washed successively with 10% HCl, $H_2O$, ethanol, acetone and ether. After drying in vacuo over $P_2O_5$ over night, the cis-dichloro-(1,2-cyclohexanediammine)-platinum (II) is stirred with an equimolar amount of silver sulfate in distilled, degassed water under nitrogen atmosphere for 36 hours in the dark. The silver chloride precipitate is removed and the filtrate is freeze dried to give cis-sulfato-DACH-platinum (II).

EXAMPLE XXIV

Cis-sulfato-DACH-platinum (II) is prepared in accordance with Example XXIII. Barium L-aspartate is prepared in situ using the appropriate dicarboxylic ligand. The cis-sulfato-DACH-platinum (II) and barium L-aspartate are combined and are agitated in a nitrogen atmosphere in the dark for 2 hours. Barium sulfate precipitate is filtered off and the filtrate is concentrated to about 2 ml. Acetone is added to the concentrated solution resulting in a white precipitate. This precipitate is further purified by successive washing with acetone and ether. The resulting product is (L-aspartaro-O,O')-(1,2-cyclohexanediammine-N,N')-platinum (II). (Turned brown at 240, decomposed at 280).

EXAMPLE XXV 5.1 mmol Cis-Pt(NH$_3$)I$_2$ is added to 5 mmol Ag$_2$SO$_4$ in 200 ml degassed, distilled water and is stirred in the dark at room temperature for 4 hours. AgI precipitate is filtered off and the filtrate is concentrated to about 80 ml. A solution of 5 mmol barium 2-[[[3,4,6-tri-O-acetyl-2-(N-acetylamino-2-deoxy-alpha-D-glucopyranosyl]amino]thioxomethyl]amino]butanedioate is prepared in situ using the appropriate dicarboxylic ligand which is prepared in accordance with Example XXII. The barium compound is combined with the cis-diammine-sulfato-platinum (II) solution and the mixture is agitated at room temperature for 2 hours. Barium sulfate precipitate is filtered off and the filtrate is concentrated to about 1 ml. Acetone is added to the concentrated solution resulting in a yellow precipitate. This precipitate is further purified by successive washing with acetone and ether. The resulting product is Diammine 2-[[[[3,4,6-tri-O-acetyl-2-(N-acetylamino)-2-deoxy-alpha-D-glucopyranosyl]amino]thioxomethyl]amino]butanedioate-O,O']-platinum (II). (Decomposed at 190).

EXAMPLE XXVI

Cis-sulfato-DACH-platinum (II) is prepared in accordance with Example XXIII. Barium 2-[[[3,4,6-tri-O-acetyl-2-(N-acetylamino)-2-deoxy-alpha-D-glucopyranosyl]amino]thioxomethyl]amino]butanedioate is prepared in situ using the appropriate dicarboxylic ligand which is prepared in accordance with Example XXII. The cis-sulfato-DACH-platinum (II) and barium 2-[[[3,4,6-tri-O-acetyl-2-(N-acetylamino)-2-deoxy-alpha-D-glucopyranosyl]amino]thioxomethyl]amino]-butanedioate are combined and are agitated in a nitrogen atmosphere in the dark for 2 hours. Barium sulfate precipitate is filtered off and the filtrate is concentrated to about 2 ml. Acetone is added to the concentrated solution resulting in a white precipitate. This precipitate is further purified by successive washing with acetone and ether. The resulting product is 2-[[[[3,4,6-tri-O-acetyl-2-(N-acetylamino)-2-deoxy-alpha-D-glucopyranosyl]amino thioxomethyl]amino]butanedioate-O,O']-(1,2-cyclohexanediammine)-N,N'-platinum (II). (Turned brown at 200, decomposed at 260).

EXAMPLE XXVII

Preparation of Barium acetamidomalonic acid—To 14.5 g (46.0 mmol) of barium hydroxide in 750 ml of water is added 10.0 g (46 mmol) of acetamidomalonic acid diethyl ester. The solution is refluxed for one hour and suction filtered while still hot. The filtrate is allowed to cool to room temperature to give barium acetamidomalonate in quantitative yield as white crystals. IR (KBr) 3366.8, 1654, 1640, 1599, 1578, 1530, 1427, 1344 cm$^{-1}$. Elemental analysis for BaC$_5$H Theoretical C(20.25), H(1.69), N(4.72)
Found C(20.02), H(1.55), N(4.56)

EXAMPLE XXVIII

Sulfato-2,2-dimethyl-1,3-propanediamine platinum (II) is prepared in the same manner as described for Cis-sulfato-DACH-platinum (II) in Example XXIII except that 2,2-dimethyl-1,3-propanediamine is used instead of 1,2-cyclohexanediamine.

EXAMPLE XXIX

Preparation of Cis-R,R-(acetamidomalonato-O,O')(1,2-cyclohexanediamine-N,N')platinum (II) (AMP)-4.704 g (11.605 mmol) of Cis-R,R-sulfato-DACH-platinum (II) (prepared as described in Example XXIII except that R,R-1,2-cyclohexanediamine is used) in 50 ml of water is added to a solution of 3.45 g (11.607 mmol) barium acetamidomalonate in 250 ml of water and the mixture is stirred in the dark under a nitrogen atmosphere for 1 hour. Barium sulfate precipitate is filtered off and the filtrate is concentrated to about 20 ml. The resulting solid is collected and washed with acetone and ether (56% yield). Decomp. point (256° C.). IR (KBr): 3292, 3? 95, 3070, 2925, 1677, 1635. 1573, 1538, 1393 cm$^{-1}$. Elemental Analysis for $C_{11}H_{19}N_3O_5Pt$ Theoretical C(28.20), H(4.08), N(8.97), Pt(41.65)
Found C(28 26), H(4.38), N(9.03), Pt(41.53)

EXAMPLE XXX

Cis-R,R-(formamidomalonato-O,O')(1,2-cyclohexanediamine-N,N') platinum (II) (FMP) is prepared in the same manner as in Example XXIX except that barium formamidomalonate was used. Decomp. point (244° C.). Elemental Analysis for $C_{10}H_{17}N_3O_5Pt$ Theoretical C(26.43), H(3.77), N(9.24), Pt(42.93)
Found C(26.21), H(3.72), N(9.03), Pt(42.09)

EXAMPLE XXXI

Preparation of Diammine (acetamidomalonato-O,O')platinum (II)-3.82 g(7.92 mmol) Cis-$(NH_3)_2PtI_2$ in 300 ml of water is added to a solution of 2.40 g (7.69 mmol) $Ag_2SO_4$ in 200 ml degassed distilled water and stirred in the dark at room temperature under a nitrogen atmosphere for 4 hours. AgI precipitate is filtered off and the filtrate is concentrated to about 200 ml. To this solution is added 2.28 g (7.66 mmol) of barium acetamidomalonate in 120 ml of water. The mixture was stirred in the dark for half an hour, filtered, and the filtrate is concentrated on a rotary evaporator to about 90 ml during which a white precipitate is formed. The product is filtered off and washed with ethanol and ether and dried over P2O5 in a vacuum desiccator (66% yield). Decomp. Point 235° C.). IR (KBr): 3428, 3358, 3247, 1688, 1640, 1403 cm$^{-1}$. Elemental Analysis for $C_5H_{11}N_3O_5Pt.1/2\ H_2O$ Theoretical C(15.13), H(3.05), N(10.58), Pt. 49.14
Found C(15.59), H(3.39), N(10.63), Pt(49.22)

EXAMPLE XXXII (Acetamidomalonato-O,O')(2,2-dimethyl1-1,3-propanediamine-N,N') platinum (II) is prepared in the same manner as in Example XXIX except that sulfato-2,2-dimethyl-1,3-propanediamine platinum (II) is used in place of Cis-R,R-sulfato-DACH-platinum (II). Elemental Analysis for $C_{10}H_{19}N_3O_5Pt.3H_2O$ Theoretical C(23.53), H(4.93), N(8.23), Pt (38.22)
Found C(23.47), H(4.92), N(8.08), Pt (34.39)

EXAMPLE XXXIII

Preparation of cis-R,R-[2-[(pentalacetylgluconyl)imino]propanedioato-O,O'](1,2-cyclohexanediammine-N,N')platinum(II). 11.4 g of pentalacetylgluconylchloride in 5 ml acetonitrile is added to a solution of 9.6 g of iminomalonic acid and 33 ml of N,N-diisopropylethylamine in 280 ml of a water-acetonitrile mixture (1:1 V/V). The resulting mixture is stirred until thin layer chromatography (CHCl3:methanol, 9:1) shows complete disappearance of gluconylchloride. Acetonitrile is removed under reduced pressure and the water layer is basified with saturated sodium bicarbonate and is then extracted with CHCl3. The aqueous layer is acidified with 10% HCl and is extracted with ethylacetate. The ethylacetate layer is backwashed with water and is dried over $Na_2SO_4$. The product is further dried through evaporation in vacuo to give [(pentalacetylgluconyl)imino] malonic acid in a 72% yield.

2.4 g of this intermediate is admixed with 1.5 g barium hydroxide.8H2O. The resultant is added to 1.9 grams of cis-R,R-sulfato-(cyclohexane-1,2-diammine-N,N')-platinum(II) which is already in solution with 200 ml of water. This mixture is stirred at room temperature for 2 hours. Next the barium sulfate is filtered off, and the resulting filtrate is evaporated under reduced pressure to yield a cyclohexane-1.2-diammine-platinum(II) salt/complex of [(pentalacetylgluconyl)imino]malonic acid ("R,R-AG-AMP").

EXAMPLE XXXIV

The compound of Example XXXIII is admixed with an isotonic solution to produce a dosage form suitable for intravenous administration. 130 mg/m$^2$ body surface area of a patient is administered to said patient through intravenous administration over a period of 24 hours.

EXAMPLE XXXV

Preparation of cis-R,R-[2-(gluconylamino)propanedioato-O,O'](1,2-cyclohexanediammine-N,N')platinum-(II). 4 g of [(pentalacetylgluconyl)imino]malonic acid, prepared as in Example XXXIII, is added to 35 ml of a mixture of triethylamine, methanol and water (in a ratio of 1:2:1) and stirred at room temperature overnight. Removal of solvents leaves a residue which is dissolved in water and treated with AMBERLYTE IR-120 H resin (Aldrich Chemical). Filtration of the resin and evaporation gives the de-acetylated product (gluconylimino)malonic acid in a 60% yield.

1 g of this intermediate is admixed with 1.06 g barium hydroxide.8H2O. The resultant is added to 1.36 grams of cisR,R-sulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to Yield a cyclohexane-1,2-diammine-platinum(II) salt/complex of (gluconylimino)malonic acid ("R,R-G-AMP").

EXAMPLE XXXVI

The compound of Example XXXV is admixed with an isotonic solution to produce a dosage form suitable for intravenous administration. 130 mg/m$^2$ body surface area of a patient is administered to said patient through intravenous administration over a period of 24 hours.

EXAMPLE XXXVII

The compound 2-[[[3,4,6-tri-O-acetyl-2-(N-acetylamino)-2-deoxy-alpha-D-glucopyranosyl]amino]-thioxomethyl]amino]butane-dioato-O,O']-[1,2-cyclohexanediammine-N,N']platinum (II) and cisplatin were tested against murine P388 leukemia. The murine P388 leukemia system is known to be sensitive to cisplatin. The leukemia was maintained intraperitoneally in female DBA/2 mice.

Prior to administration, cisplatin was dissolved in sterile saline (0.85% sodium chloride). The compound 2-[[[3,4,6-tri-O-acetyl-2-(N-acetylamino)-2-deoxy-alpha-D-glucopyranosyl]amino]-thioxomethyl]amino]-butanedioato-O,O']-[1,2-cyclohexanediammine-N,N']platinum (II) was dissolved in sterile water at 4° C. immediately prior to administration.

Each compound was administered intraperitoneally to groups of $CD2F_1$ male mice on day 1 after intraperitoneal implantation of $1 \times 10^6$ P388 leukemia cells. P388 antileukemic activity for each compound was assessed by mean survival days and percentage increased life span (%ILS).

%ILS is calculated as follows:
%ILS=(T-C)/C×100
wherein T is the mean survival days of the treated mice and C is the mean survival days of the untreated mice. The results of the experimentation are shown in the following table.

TABLE 2

| Compound | Dose | % ILS | Mean Survival (days) |
|---|---|---|---|
| cisplatin | 10 mg/kg | 96 | 15.7 |
| invention | 400 mg/kg | 76 | 14.1 |
| invention | 800 mg/kg | toxic | — |

EXAMPLE XXXVIII
Murine Toxicity Studies

| Compound | Single Dose (intraperitoneal) | Day 3 WBC Count* (% of Control) | BUN on Day 4 (mg/dl) mean + S.D. | Creatinine on Day 4 (mg/dl) mean + S.D. |
|---|---|---|---|---|
| AMP | 150 mg/kg | 78% | 30.8 ± 4.8 | 0.3 ± 0.1 |
| Control-drug vehicle | | | 23.5 ± 2.1 | 0.1 |

*Peripheral leukocyte (WBC) count, BUN and creatinine performed on normal CD2F male mice on Day 3 or 4 post drug administration.

EXAMPLE XXXIX
Murine Antitumor Activity

| Compound | Single Dose (intraperitoneal) | Deaths Due to Drug Toxicity | P388 Antitumor Activity: % ILS* |
|---|---|---|---|
| AMP | 150 mg/kg | | 115% |
| | 200 mg/kg | 1/10 | 93% |
| | 250 mg/kg | 5/10 | |
| FMP+ | 150 mg/kg | | 84% |
| | 200 mg/kg | | 115% |
| | 250 mg/kg | 2/10 | 81% |
| R,R-AG-AMP | 150 mg/kg | 0/10 | 75% |

*P388 cells implanted intraperitoneally (i.p.) into male $CD2F_1$ mice on Day 0. Drugs (in 5% dextrose) administered i.p. on Day 1. Increase in life span (% ILS) was calculated compared to a group of mice receiving drug vehicle, with a mean survival of 8.5 days.
+compound was administered as a suspension.

What is claimed is:

1. A compound of the formula $$\begin{array}{c} \text{(CH}_2)_n\text{—COO} \diagdown \diagup \text{NH}_2\text{R}_2 \\ \text{O} \quad | \quad \text{Pt} \\ \| \quad | \diagup \diagdown \\ \text{R—C—N—CH——COO} \quad \text{NH}_2\text{R}_3 \\ | \\ \text{R}_1 \end{array} \quad (I)$$

wherein n is 0 or 1 and when n is 1, $R_1$ is H or $C_1$–$C_4$ alkyl, R is non-substituted higher alkyl or mono or disaccharide or a derivative of a mono or disaccharide, when n is 0, $R_1$ is H or $C_1$–$C_4$ alkyl, R is H, halogen, non-substituted $C_{1-20}$ alkyl, aryl, aralkyloxy, mono or disaccharide, or a derivative of a mono or disaccharide, and $R_2$ and $R_3$ are selected from the group consisting of hydrogen, $C_{1-4}$ alkyl or $R_2$ and $R_3$ together are linked to adjacent carbon atoms on a four, five or six membered ring structure, or $R_2$ and $R_3$ together form a fused or bicyclic ring with adjacent carbon atoms, or $R_2$ and $R_3$ together are an alkylene group to form a ring of from 4 to 8 members; with the proviso that R and $R_1$ cannot both be hydrogen when n=0, or a pharmaceutically acceptable salt thereof.

2. A compound of claim 1, wherein $R_2$ and $R_3$ are hydrogen.

3. A compound of claim 1, wherein $R_2$ and $R_3$ together are linked to adjacent carbon atoms on a four, five or six membered ring structure.

4. A compound of claim 1, wherein $R_2$ and $R_3$ together form a fused or bicyclic ring with adjacent carbon atoms.

5. A compound of claim 1, wherein $R_2$ and $R_3$ together form a group of the following formula:

$$\diagdown_{C} \bigcirc (CH_2)_{n_1} \diagup$$

wherein $n_1$ is selected from 1, 2, 3, 4, 5 or 6.

6. A compound of claim 1, wherein $R_2$ and $R_3$ together form a group of the following formula:

$$\begin{array}{c} \diagdown \\ \text{CH} \\ | \quad \bigcirc (CH_2)_{n_1} \\ -\text{CH} \\ \diagup \end{array}$$

wherein $n_1$ is selected from 1, 2, 3, 4, 5 or 6.

7. A compound of claim 1, wherein said compound is of the formula $$\begin{array}{c} \text{O} \\ \| \\ \text{(CH}_2)_n\text{—C—O} \diagdown \diagup \text{NH}_2 \\ \text{O} \quad | \quad \text{Pt} \quad (CH_2)_{n'}\text{—R}_4 \\ \| \quad | \quad \| \diagup \diagdown \\ \text{R—C—N—CH——C—O} \quad \text{NH}_2 \\ | \quad \| \\ \text{R}_1 \quad \text{O} \end{array}$$

and $R_1$ and R are defined as in claim 1, n' is 1, 2, 3, 4 or 5 and $R_4$ is hydrogen, halogen, aryl or $C_{1-20}$ alkyl.

8. A compound of claim 1, wherein said compound is cis R,R-(acetamidomalonato-O,O')(1,2-cyclohexanediamine-N,N') platinum (II).

9. A compound of claim 1, wherein said compound is cis-R,R-(formamidomalonato-O,O')(1,2-cyclohexanediamine-N,N') platinum (II).

10. A compound of claim 1, wherein said compound is diammine (acetamidomalonato-O,O') platinum (II).

11. A compound of claim 1, wherein said compound is (acetamidomalonato-O,O')(2,2-dimethyl-1,3-propanediamine-N,N') platinum (II).

12. A compound of claim 1, wherein $R_2$ and $R_3$ together form an unsubstituted $C_{1-5}$ alkylene chain.

13. A compound of claim 1, wherein the compound is cis-R,R-[2-[(pentalacetylgluconyl)imino]propanedioato-O,O'](1,2-cyclohexanediammine-N,N')platinum-(II).

14. A compound of claim 1, wherein the compound is cis-R,R-[2-(gluconylimino)propanedioato-O,O'](1,2-cyclohexanediammine-N,N')platinum(II).

* * * * *